(12) United States Patent
Kuo

(10) Patent No.: US 6,836,680 B2
(45) Date of Patent: Dec. 28, 2004

(54) DETECTOR FOR MEASURING ELECTROCARDIOGRAM, PULSE AND VOICE SOUND AT THE SAME TIME

(75) Inventor: Terry B. J. Kuo, 7F-2, No. 52, Peichang 5 St., 30 Lin, Peichang Tsun, Chian Hsiang, Hualien Hsien (TW)

(73) Assignees: Leadtek Research Inc., Taipei Hsien (TW); Terry B. J. Kuo, Hualien Hsien (TW)

( * ) Notice: Subject to any disclaimer, the term of this patent is extended or adjusted under 35 U.S.C. 154(b) by 521 days.

(21) Appl. No.: 10/047,764

(22) Filed: Jan. 15, 2002

(65) Prior Publication Data

US 2003/0135126 A1 Jul. 17, 2003

(51) Int. Cl.[7] .................................................. A61B 5/04
(52) U.S. Cl. ........................ 600/513; 600/483; 600/586
(58) Field of Search ................................ 600/382, 387, 600/393, 483, 484, 500, 501, 504, 509, 513, 514, 519, 521, 522, 528, 529, 532, 538, 586

(56) References Cited

U.S. PATENT DOCUMENTS

| | | | | |
|---|---|---|---|---|
| 3,773,033 A | * | 11/1973 | Rodbard et al. | 600/500 |
| 4,452,252 A | * | 6/1984 | Sackner | 600/484 |
| 4,519,399 A | * | 5/1985 | Hori | 600/537 |
| 5,732,700 A | * | 3/1998 | Lundback | 600/387 |
| 5,913,829 A | * | 6/1999 | Reeves et al. | 600/528 |
| 6,423,013 B1 | * | 7/2002 | Bakker et al. | 600/586 |
| 6,607,492 B2 | * | 8/2003 | Ogura | 600/485 |

* cited by examiner

Primary Examiner—Jeffrey R. Jastrzab
Assistant Examiner—Frances P. Oropeza
(74) Attorney, Agent, or Firm—J.C. Patents

(57) ABSTRACT

The analyzing system of the present invention, taking electrocardiogram, pulse signals and sound voices from the outside of the body, is readily assessable and complete in function. The analyzing system of the present invention can provide physiological indexes for evaluating the functions of the heart, vocal chord, the respiration system and the autonomic nervous system. The measured signals and obtained data can be on-line analyzed or sent to computer systems for an off-line verification after the completion of the test. Through digital or wireless communications, a rapid on-line diagnosis can be achieved for mitigating potential consequences.

17 Claims, 11 Drawing Sheets

ECG, PULSE, AND SOUND COMBINED SENSOR

ECG, PULSE, AND SOUND COMBINED SENSOR

DETECTOR FOR MEASURING ELECTROCARDIOGRAM, PULSE AND VOICE SOUND AT THE SAME TIME

BACKGROUNDING OF THE INVENTION

1. Field of Invention

The present invention relates to a detector system. More particularly, the present invention relates to a detector system for measuring the electrocardiogram, pulse and voice sound at the same time and its analytical system.

2. Description of Related Art

Almost the function of every organ can be monitored and measured because of the advances in science nowadays. However, most developed techniques are invasive. For example, the cardiovascular checkup needs to put a pipe into the heart through the main artery, which is dangerous and painful to the testee (patient).

Compared with the invasive techniques, non-invasive techniques are not that painful and distressing to patients. But non-invasive techniques sometimes are not accurate and practical enough, due to its inability of entering into the human bodies.

Because of the recent developments in signal detection and processing, it is possible to strengthen the non-invasive techniques by implementing mathematical manipulation of computers. One representative example of the non-invasive techniques is the analysis of heart rate variability (HRV).

The analysis of HRV is to analyze small variances of the heart rate for human body in rest, which can be used to monitor the autonomic nervous system. In other words, it is attempted to analyze or evaluate the function of the autonomic nervous system without disturbing the normal life of the patient. In the conventional processes, standard chest electrocardiograms are used for the HRV analysis.

The autonomic nervous system (ANS) regulates individual organ function and homeostasis, such as heart beat, digestion, breathing and blood flow, and for the most part is not subject to voluntary control. These involuntary actions are controlled by the opposite actions of the two divisions of the autonomic nervous system—the sympathetic and the parasympathetic divisions. Most organs receive impulses from both divisions and under normal circumstances and they work together for proper organ function and adaptation to the demands of life. Problems will occur when the autonomic nervous system is out of balance, causing, for example, coronary heart disease, hypertension, digestive disturbances and even sudden death.

Many techniques have been successfully developed to assess the autonomic nervous system. Among the different techniques in assessing the autonomic nervous system, HRV is an important breakthrough because this technique is noninvasive. Moreover, animal and clinical studies confirm HRV accurately reflects the sympathetic and parasympathetic activities and their balance.

For a health adult, except for the rhythmic heartbeats: about 70 heart beats per minute, there are beat-to-beat time interval variations. The heart rate variations can be regular (periodic) or irregular, as either speeding up or slowing down. Because these variations are small in amplitudes, they were often omitted in the past. According to previous researches, some of these minor periodic variations relate to the respiration, while some variations are irrelevant to the respiration.

Recent developments in electrical engineering have enabled the assessment of heart rate variability by frequency domain analysis, which bases on mathematical manipulations performed on the data. Investigators have discovered that, based on frequency analysis, HRV can be characterized into two main components: the high frequency (HF) component and the low frequency (LF) component. The high frequency component is equivalent to respiratory sinus arrhythmia and is considered to represent the influence of the vagal control of the heart rate. The exact origin of the low frequency component is not known. It is probably related to vessel activity or baroreflex. Some investigators further divide the low frequency component into a low frequency component and a very low frequency component. Many physiologists and cardiologists believe that the high frequency (HF) component or the total power (TP) can consider representing the parasympathetic control of the heart rate and the ratio LF/HF is considered to mirror the sympathovagal balance or to reflect the sympathetic modulations.

It is well documented that HRV is clinically valid and meaningful in reflecting many physiological functions. Reduced HRV appears to be a marker of an increase of intra-cranial pressure. A recent study by Framingham further indicates that if the HRV of an elderly is lowered by one standard deviation, his (her) mortality rate is about 1.7 times higher than a normal individual.

The voice sound generated from the vocal chord is not only a tool of communications, but also useful in assessing respiratory diseases like flues. Therefore, the voice sound can be used as an index of non-invasive diagnostic techniques.

There are two major fields in the development of non-invasive diagnostic techniques, one is about the detector system and the other field is focused on digital signal processing. The most important of all, the detector system needs to be accurate in obtaining data and convenient for the users.

SUMMARY OF THE INVENTION

Accordingly, the present invention provides a detector system for measuring the electrocardiogram, pulse and voice sound at the same time. The provided detector system is both comfortable and easy to use, thus promoting the application of this non-invasive diagnostic technique. The measured electrocardiogram signal and pulse signal are digitally processed to obtain quantitative values of the ANS activity, along with the analyzed result of the voice sound signal, for monitoring and diagnosing the diseases.

Accordingly, the present invention provides a three-in-one detector system that can measure the signals of electrocardiogram, pulse and voice sound from outside the human body (from the neck) in a non-invasive way. The measured results are further analyzed to transform the signals of electrocardiogram and pulse into indexes for accessing the function of the autonomic nervous system.

The present invention provides a detector system for measuring the basic physiological signals of electrocardiogram, pulse and voice sound at the same time and a corresponding analyzing system. The obtained signals are digitally processed and transformed into physiological indexes for monitoring functions of the heart, autonomic nervous systems, the vocal chord and respiration systems. The detector system is easy to operate, painless and be used at the convenience of the user. The obtained physiological indexes can be on-line analyzed or stored for later off-line analysis. Digital communications and the internet network can be applied to assist the analysis of the data for communicative diagnosis or monitoring. The present invention further provides a complete and multifunction analyzing system, which can analyze the measured electrocardiogram and pulse signals for monitoring the ANS function.

Since the detector system measuring the signals from the outside of the body (from the neck) is not heavy or complicated, the subject's normal life and movements will not be hampered by the provided system. In combination with wireless communication, the detector system of the present invention can be portable and become a personalized system, unlike the conventional chest electrocardiogram detector.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings, FIG. 1A is a display diagram illustrating the structure of the detector system according to one preferred embodiment of the present invention, while

DESCRIPTION OF THE PREFERRED EMBODIMENTS

Figure 1A:
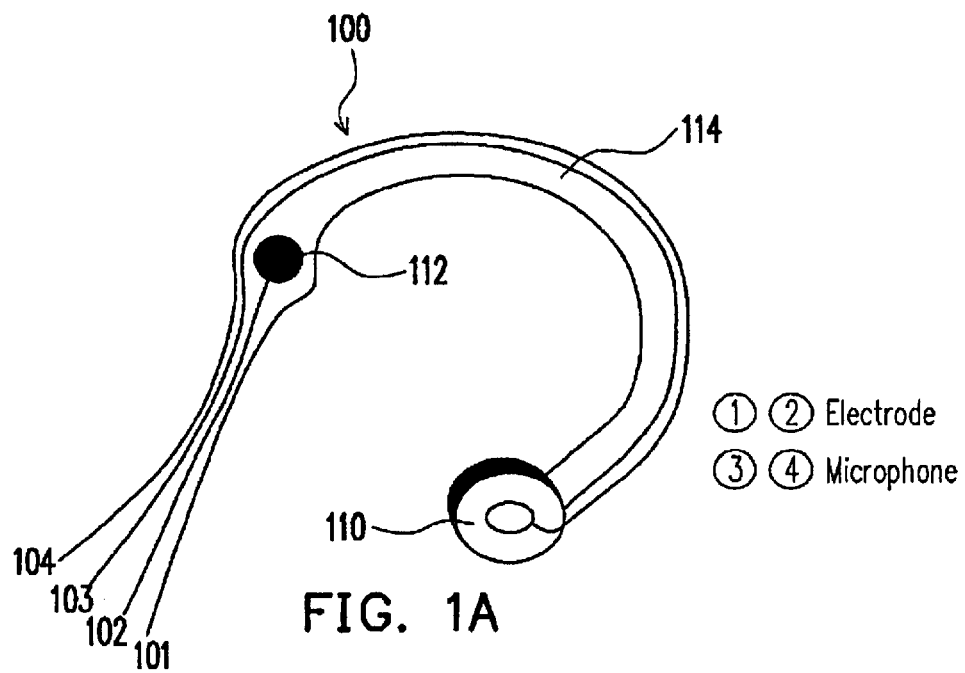
Figure 1B:
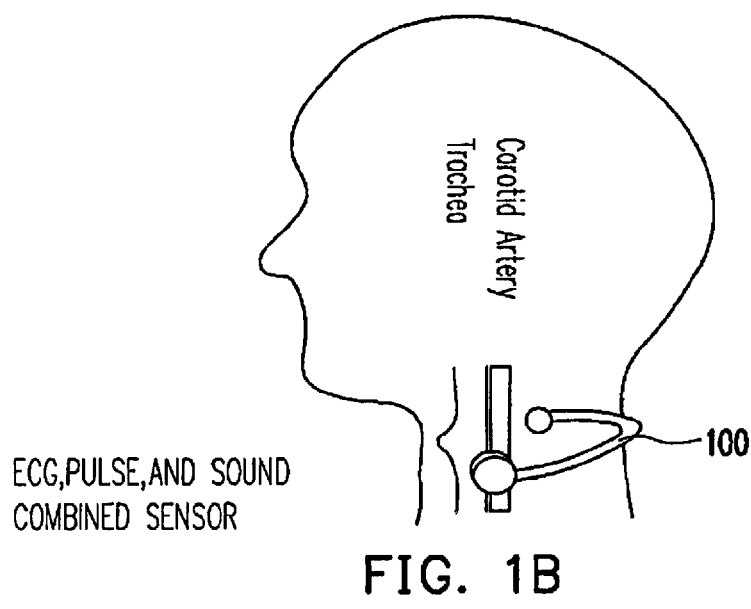
FIG. 1B is a display diagram illustrating the usage of the detector system according to one preferred embodiment of the present invention.
Figure 2:
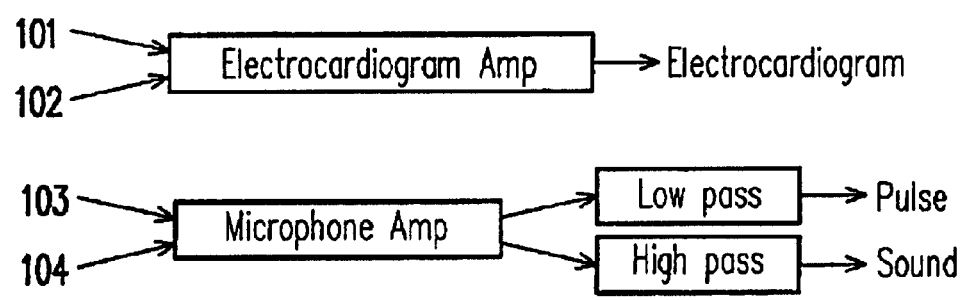
FIG. 2 is a flow diagram illustrating the theory of the detector system according to one preferred embodiment of the present invention.

FIG. 1A is a display diagram illustrating the structure of the detector system according to one preferred embodiment of the present invention, while FIG. 1B is a display diagram illustrating the usage of the detector system according to one preferred embodiment of the present invention. The detector system 100 includes one microphone 110 and two electrodes 112, and a flexible framework 114 is used to integrate the microphone and the electrodes. These two electrodes are connected through two wires 101, 102 to the external, while the microphone is outputted through two wires 103, 104. However, the casing of the microphone can be integrated with one electrode, so that wire 101 is merged with wire 103, leaving only three wires.

As shown in FIG. 1B, the detector system 100 is placed on (collared to) the neck of the user and the microphone is disposed aside of the trachea, which location is above the passage of the carotid artery. The detector system can clip to the neck as a neckband and both ends of the detector system are placed on opposite sides of the neck. Because the framework is flexible, it can provide adequate pressure to keep the microphone and electrodes in close contact to the neck.

The detector system further includes amplifiers, high pass filters, low pass filters and analog-to-digital (A/D) converters. The design of these devices may vary depending on the user's demand or according to the coupling analyzing system. The techniques well known to one skilled in the art at the present time can be applied to the present invention and are within the scope of the present invention.

The detector system of the present invention collects the electrocardiogram, pulse and voice sound signals at the same time. Normally the collection time is 5 minutes. After amplifying and passing through filters, the electrocardiogram, pulse and voice sound signals are further transmitted to an analog-to-digital (A/D) converter with a sampling rate ranged from 256 to 44000 Hz. The acquisition of data and the subsequent data analysis are accomplished with a computing device, which includes portable computer, personal digital assistant (PDA) and microchips like those used in mobile phones and watch. The computing system must comprise also a microprocessor and adequate memory. The digitized sound signals can be analyzed on-line during a study and simultaneously stored in removal hard disks for off-line verification after the completion of the study.

Figure 4:
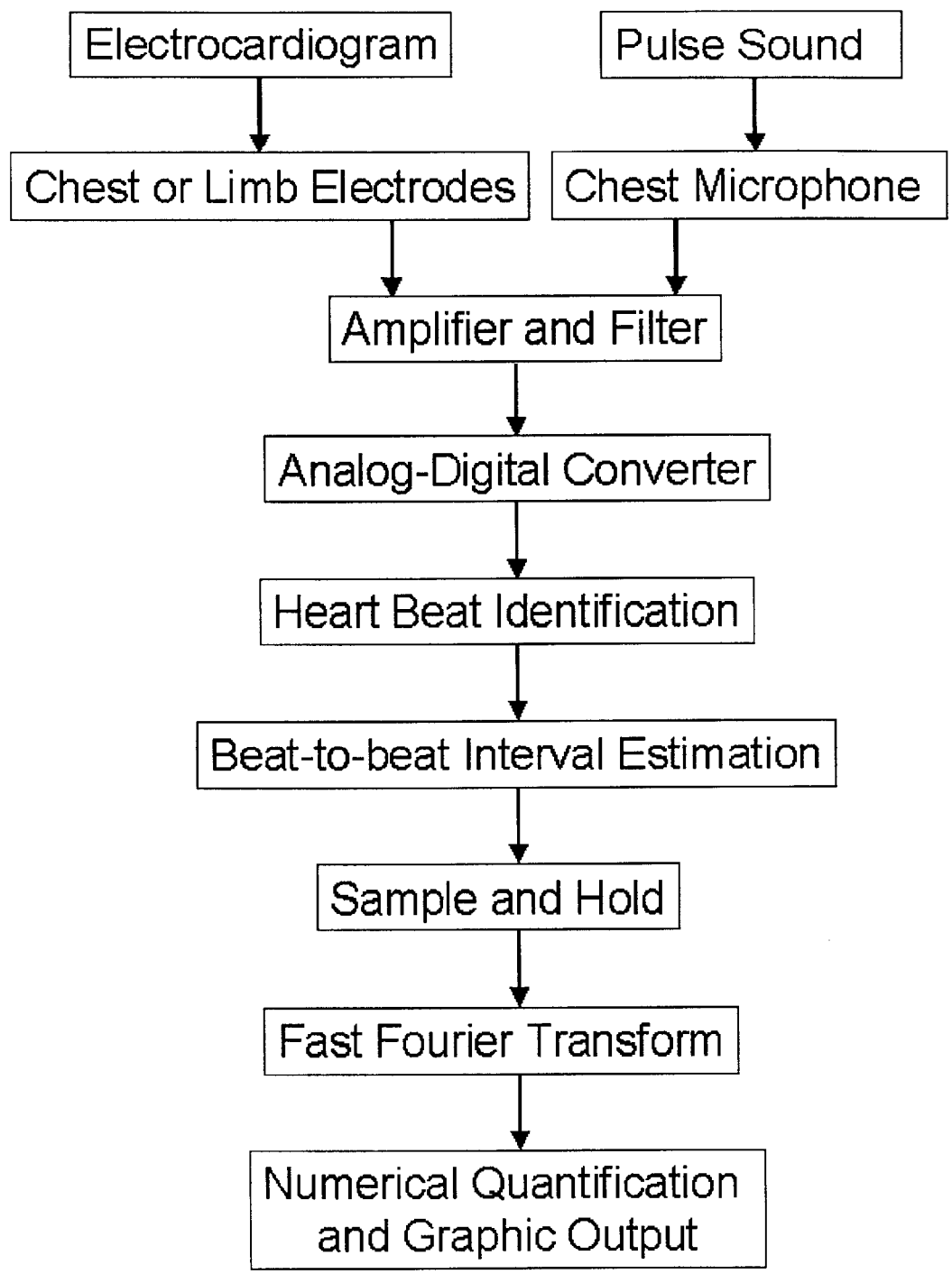
FIG. 4 illustrate the approach for the detector system to collect, process and analyze the electrocardiogram, pulse and sound voice signals according to one preferred embodiment of the present invention.

FIG. 4 illustrate the approach for the detector system to collect, process and analyze the electrocardiogram, pulse and sound voice signals according to one preferred embodiment of the present invention.

Pulse Collection

Figure 3:
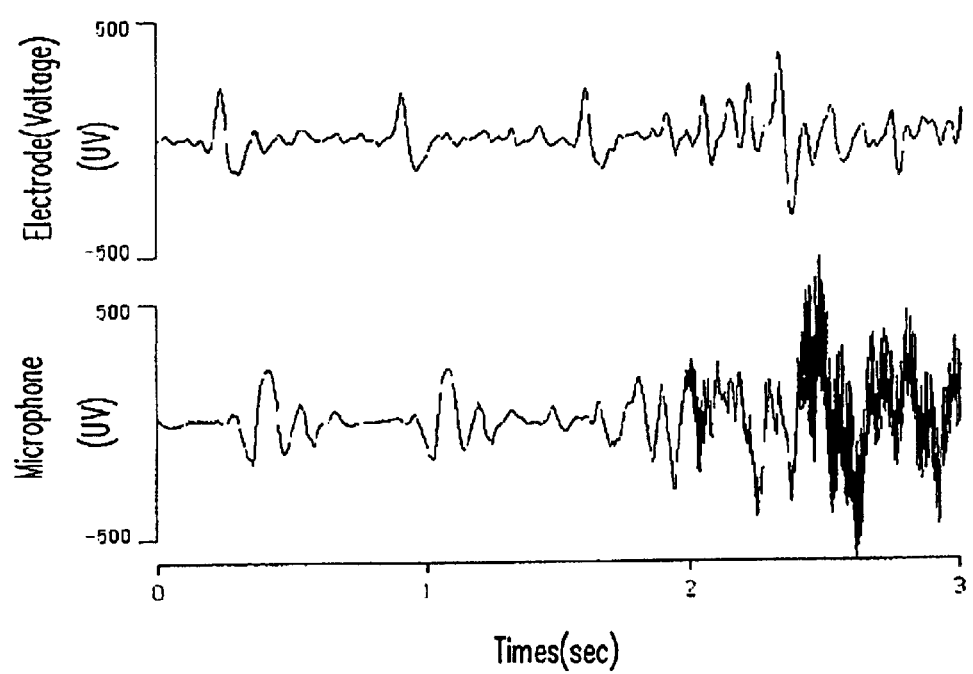
FIG. 3 illustrates a electrocardiogram and a sound spectrogram measured by the detector system in a three-second study on a subject according to one preferred embodiment of the present invention.

FIG. 3 illustrates a electrocardiogram and a sound spectrogram measured by the detector system in a three-second study on a subject according to one preferred embodiment of the present invention. The electrocardiogram is obtained from the electrode, while the sound spectrogram containing the pulse and voice sound signals is obtained from the microphone. From the sound spectrogram, the pulse signal is present from second 0 to second 2, while the voice sound signal is obtained from second 2 to second 3 from speaking of the testee.

The microphone is disposed above the carotid arteries for collecting the pulse sound and vibration. Through a conventional amplifier in the microphone, applicable signal/noise ratio can be obtained as shown in the bottom left part of FIG. 3. A low pass filter can be further included to filter out the high frequency noises.

Voice Sound Collection

The microphone is disposed adjacent to the trachea for collecting the voice sound and vibration during speaking. Through a conventional amplifier in the microphone, applicable signal/noise ratio can be obtained as shown in the bottom right part of FIG. 3. A high pass filter can be further included to filter out the low frequency noises.

Electrocardiogram Collection

Two electrodes in the detector system consist of a basic circuit for collecting electric signals. Di-electrode input, rather than tri-electrode differential input, is adopted in the present invention, possibly causing serious noise interference. However, an amplifying circuit can be used to amplify the electrocardiogram input of two electrodes, in order to obtain applicable signal/noise ratio as shown in the upper part of FIG. 3.

Heart Beat Identification

The digitized signals are analyzed to identify the heartbeats and estimate the beat-to-beat intervals. Digital signal processing, including frequency domain analysis, time domain analysis and non-linear analysis, is applied to further interpret the data into physiologically meaningful information.

Figure 5:
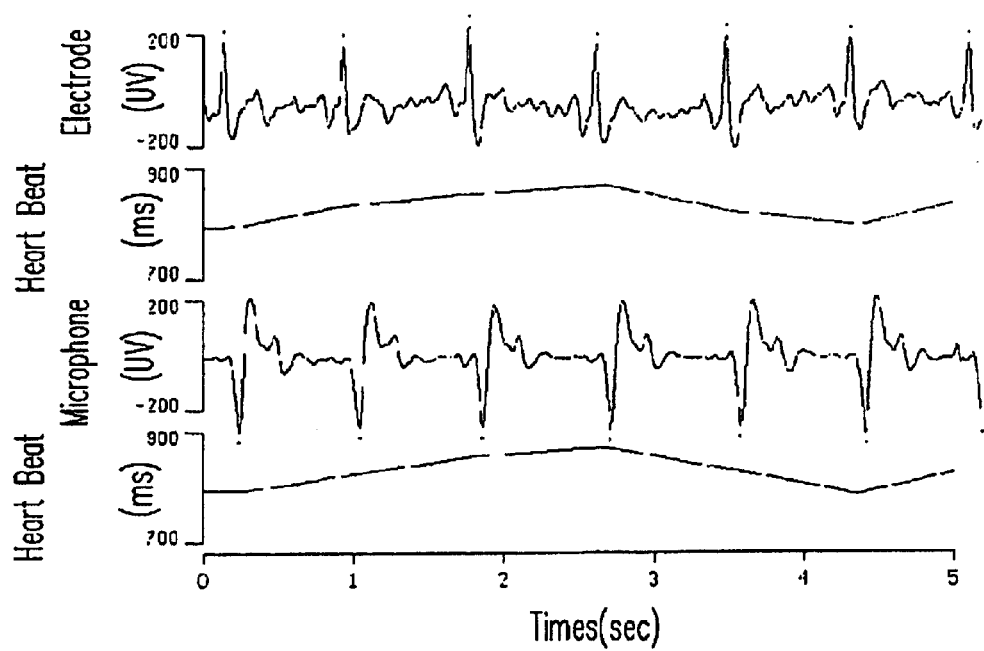
FIG. 5 illustrates the electrocardiogram and the sound spectrogram measured by the detector system and the corresponding beat-to-beat intervals in a five-second study on a subject according to one preferred embodiment of the present invention. The dots indicate the peaks of the heart rate automatically identified by a computer.
Figure 6:
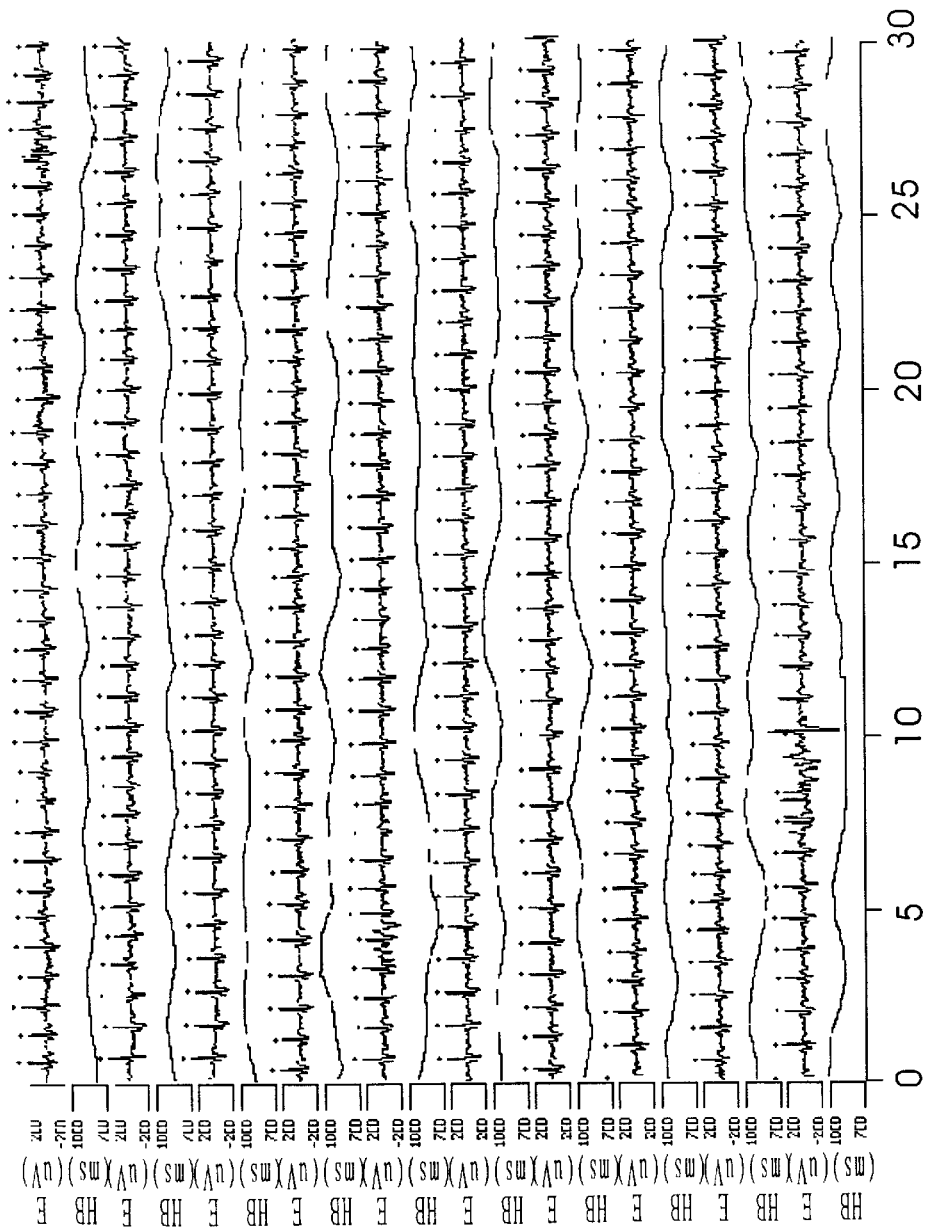
FIG. 6 illustrates the electrocardiogram measured by the detector system and the corresponding beat-to-beat intervals in a five-minute study on a subject according to one preferred embodiment of the present invention. The dots indicate the peaks of the heart rate automatically identified by a computer.
Figure 7:
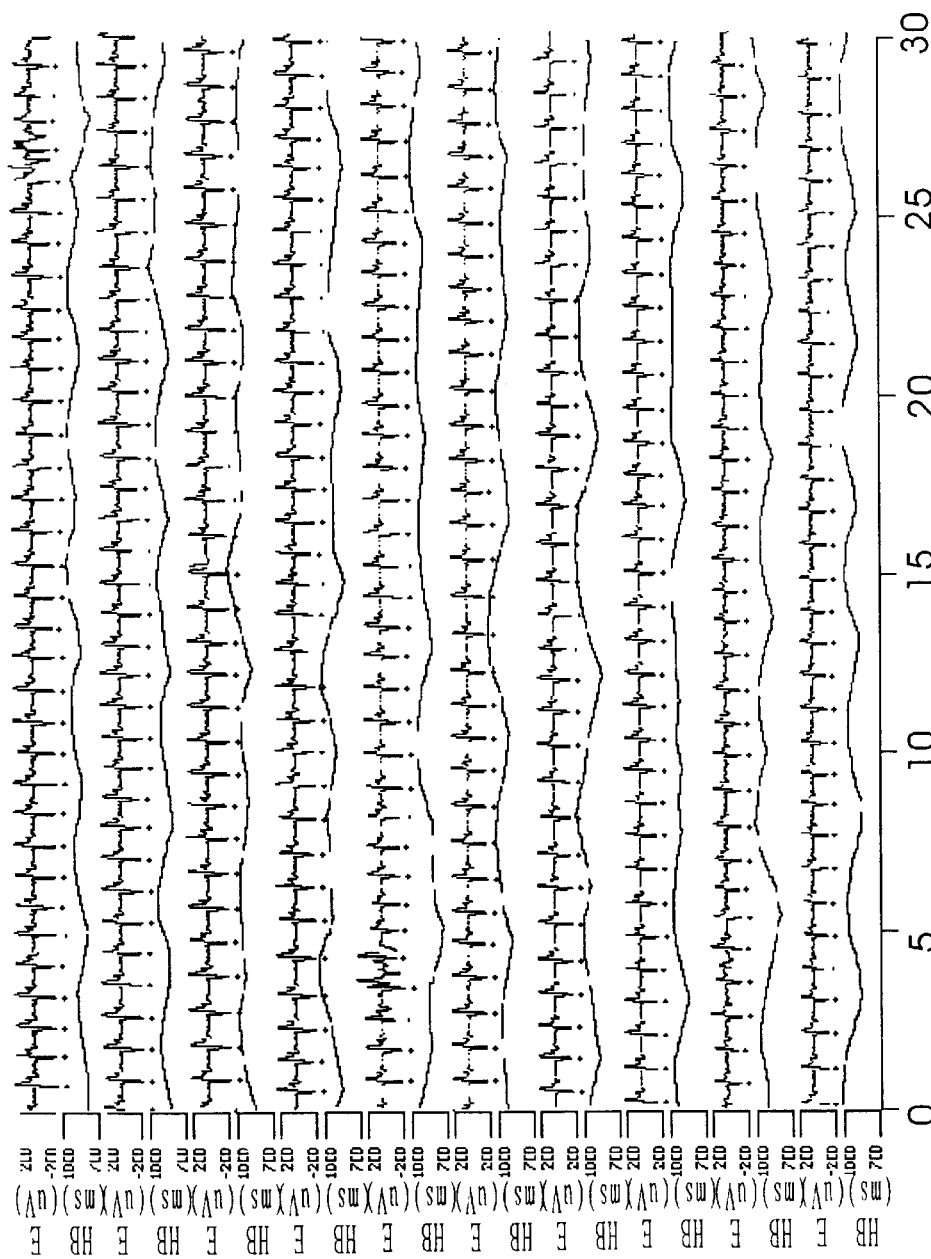
FIG. 7 illustrates the sound spectrogram measured by the detector system and the corresponding beat-to-beat intervals in a five-minute study on a subject according to one preferred embodiment of the present invention. The dots indicate the peaks of the heart rate automatically identified by a computer.

A spike detection algorithm is used to detect all peaks of the digitized sound signals. The peak of each heartbeat is defined as the time point of the heart beat, and the interval between two peaks is estimated as the beat-to-beat interval between current and latter heartbeats. FIG. 5 illustrates the electrocardiogram and the sound spectrogram measured by the detector system on the user's neck and the corresponding beat-to-beat intervals in a five-second study according to one preferred embodiment of the present invention. The dots indicate the peaks of the heart rate automatically identified by a computer. FIG. 6 illustrates the electrocardiogram measured by the detector system and the corresponding beat-to-beat intervals in a five-minute study. The dots indicate the peaks of the heart rate automatically identified by a computer. Similarly, FIG. 7 illustrates the sound spectrogram measured by the detector system and the corresponding beat-to-beat intervals in a five-second study. The dots indicate the peaks of the heart rate automatically identified by a computer Parameters such as amplitude and duration of all peaks are measured so that their means and standard deviations can be calculated as standard templates. Each peak of heartbeat is then compared and validated with the standard templates. If the standard score of any of the peak values exceeds three, it is considered erroneous and is rejected. Next, the intervals between two peaks (the beat-to-beat intervals) are measured so that their means and standard deviations can be calculated as standard templates. Each beat-to-beat interval is then compared and validated with the standard templates. If the standard score of any of the interval values exceeds three, it is considered erroneous and is rejected.

Frequency Domain Analysis

The validated peak interval values are subsequently resampled and interpolated at the rate of 7.11 Hz to accomplish the continuity in time domain. Thereafter, frequency-domain analysis is performed using fast Fourier transform (FFT). The DC component of the signals is deleted, and a Hamming window is used to attenuate the leakage effect. For each 288 seconds or 2048 data points, the power spectral density is estimated on the basis of fast Fourier transform. The resulting power spectrum is corrected for attenuation resulting from the sampling and the Hamming window.

Figure 8:
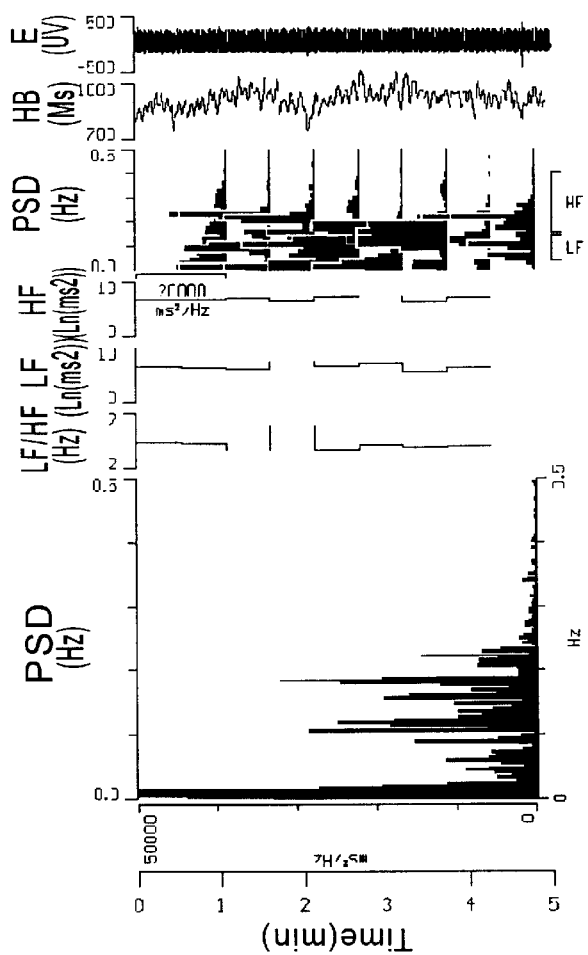
FIGS. 8 and 9 illustrate the various frequency-domain parameters for characterizing HRV based on the analysis of information shown in FIGS. 6 and 7 respectively.
Figure 9:
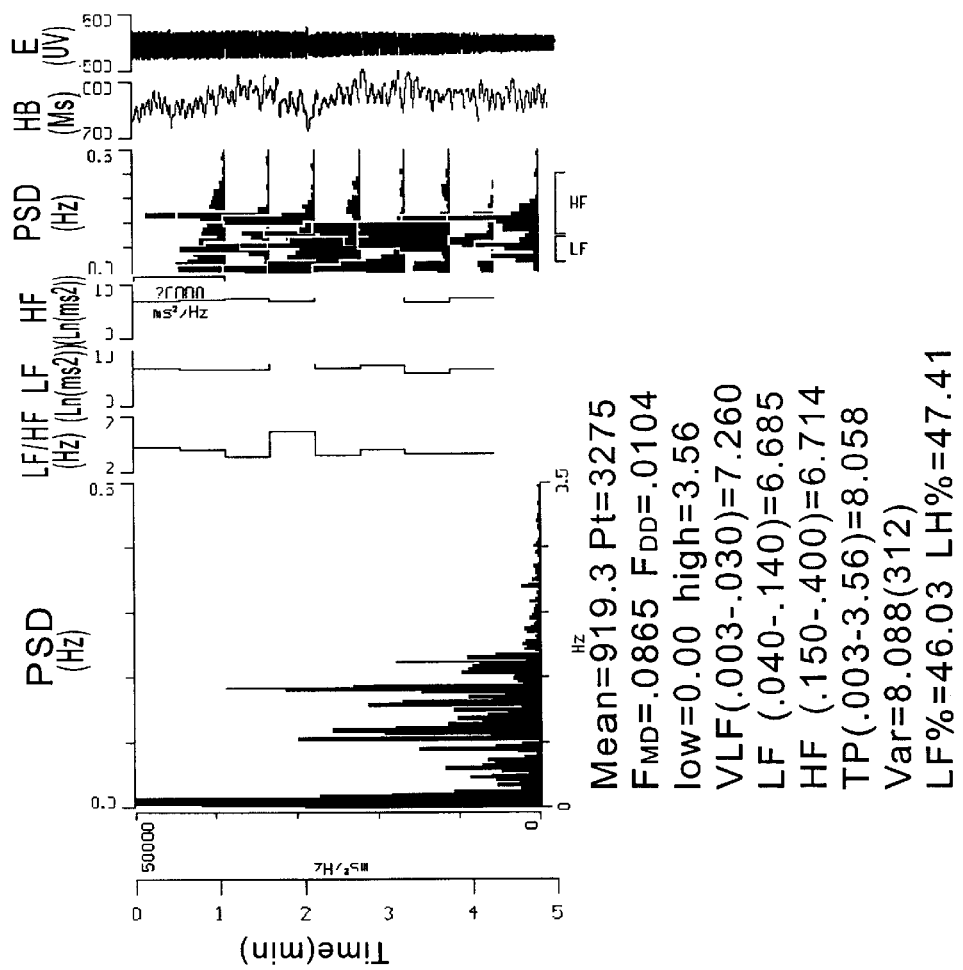

The power spectrum density (PSD) is subsequently quantified by means of integration into standard frequency-domain parameters including low-frequency (LF 0.04–0.15 Hz) and high-frequency (HF 0.15–0.40 Hz), total power (TP) and ratio of low frequency to high frequency (LF/HF). LF, HF, TP, and LF/HF are logarithmically transformed to correct for the skewness of distribution. FIGS. 8 and 9 illustrate the various frequency-domain parameters based on the analysis of information shown in FIGS. 6 and 7 respectively. The corresponding beat-to-beat intervals, power spectral density, HF, LF, HF/LF of a subject are illustrated.

The Analysis

High frequency (HF) and total power (TP) are regarded as indexes for the activity of the sympathetic division, while LF/HF is regarded as an index for the activity of the parasympathetic division. Low frequency (LF) can be sued as an integrated index for the function of both the sympathetic and the parasympathetic divisions.

Figure 10A:
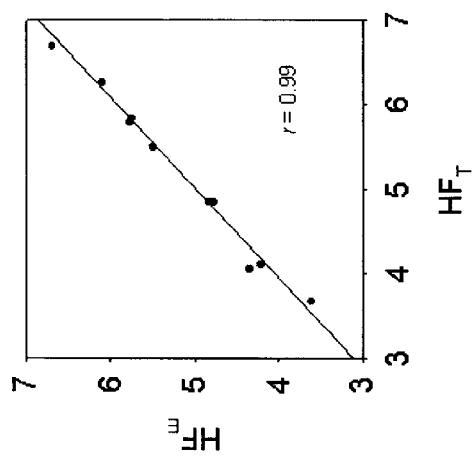
FIG. 10A shows the correlation of the various parameters that are obtained from the electrocardiogram in frequency domain on 10 control subjects obtained according to the method of the present invention ($TP_E$, $HF_E$, $LF_E$, and $LF/HF_E$) and the conventional method using lead II electrocardiogram ($TP_T$, $HF_T$, $LF_T$, and $LF/HF_T$).
Figure 10A:
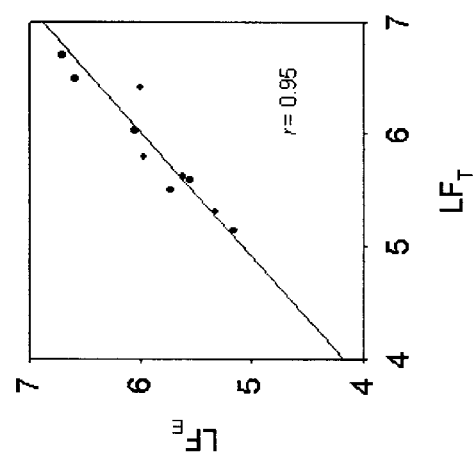
Figure 10A:
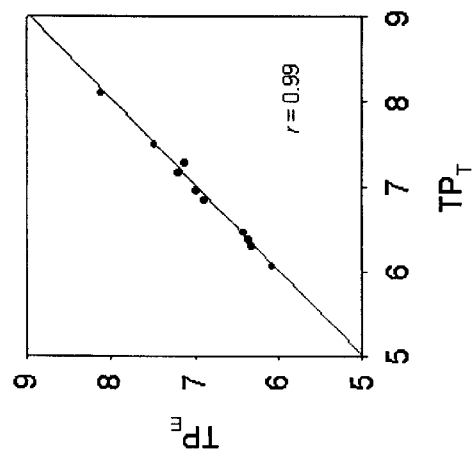
Figure 10A:
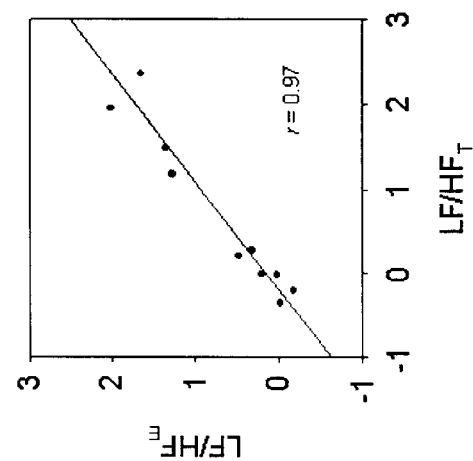
Figure 10B:
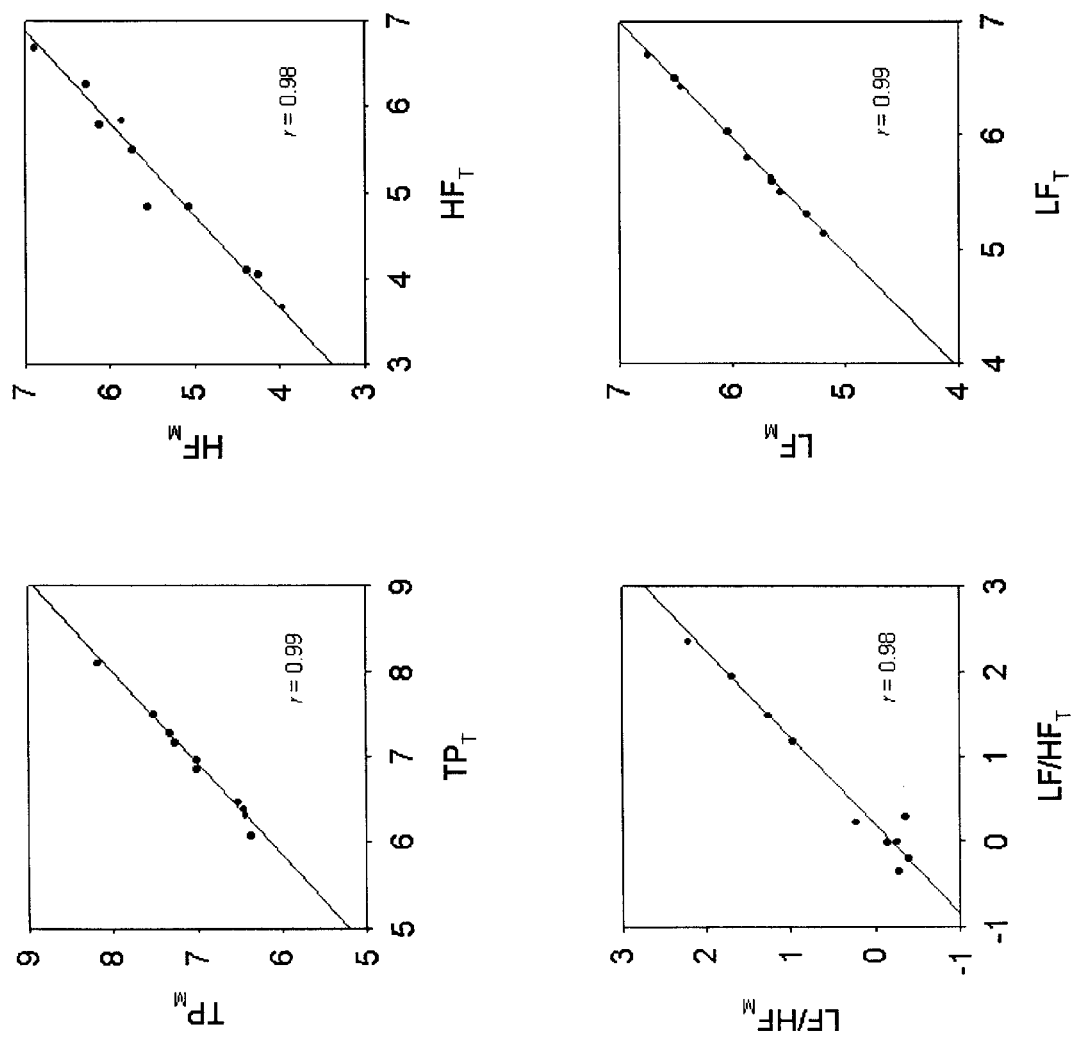
FIG. 10B shows the correlation of the various parameters that are obtained from the sound spectrogram in frequency domain on 10 control subjects obtained according to the method of the present invention ($TP_M$, $HF_M$, $LF_M$, and $LF/HF_M$) and the conventional method using lead II electrocardiogram ($TP_T$, $HF_T$, $LF_T$, and $LF/HF_T$).

FIG. 10A shows the correlation of the various parameters that are obtained from the electrocardiogram in frequency domain on 10 control subjects obtained according to the method of the present invention ($TP_E$, $HF_E$, $LF_E$, and $LF/HF_E$) and the conventional method using lead II electrocardiogram ($TP_T$, $HF_T$, $LF_T$, and $LF/HF_T$). FIG. 10B shows the correlation of the various parameters that are obtained from the sound spectrogram in frequency domain on 10 control subjects obtained according to the method of the present invention ($TP_M$, $HF_M$, $LF_M$, and $LF/HF_M$) and the conventional method using lead II electrocardiogram ($TP_T$, $HF_T$, $LF_T$, and $LF/HF_T$). From the comparison, all parameters exhibit good correlation with correlation coefficient (r)>0.93. Therefore, the detector system of the present invention can successfully obtain the ANS indexes through the electrocardiogram and pulse signals measured from the neck.

The technique and the system used in the present invention can be applied to diagnose levels of anesthesia, brain death, aging and gender variation.

The three-in-one detector system of the present invention takes electrocardiogram and pulse signals from the outside of the body to evaluate the function of the autonomic nervous system. The detector system of the present invention is readily assessable and complete in function. Moreover, the voice sound signal can be used to diagnose respiratory diseases.

In combination with conventional monitoring system, the user can monitor the ANS function or other physiological conditions either at home, in the hospital or in the caring center.

In addition, the digitized data and the corresponding HRV information, even they are collected at the patient's own home, can be sent to computer systems for an off-line verification after the completion of the test. With a rapid diagnosis and transfer of information, potential consequences are mitigated and the survivability of a patient is enhanced.

The detector system of the present invention can also be used as an input tool of conventional monitoring system. For the patients, it is convenient and painless to measure the electrocardiogram, pulse and sound signals by collaring to the user's neck.

The detector system and the analyzing system of the present invention can be promoted toward individuals, by applying the personal computer or PDA, to become a personalized monitoring system. The analyzed results can be viewed on-line by the user during the test or sent to other computer systems for an off-line verification after the completion of the test.

The three-in-one detector system can be further included in microchips like those used in mobile phones and watch, so that the mobile phones or watches become personal detector system or monitoring system.

The detector system and the analyzing system of the present invention have at least the following advantages:
1. The structure is lightweight and not complicated, which can be portable and low cost.
2. The interfaces applied in the present invention are compatible with the existing techniques, so that the system can be easily personalized or promoted toward individuals and families.
3. The system of the present invention can be easily tailed according to the user's demand and is compatible with other diagnostic software.
4. In combination with future wireless communication techniques, it is possible to apply the present system for long distance diagnosis or medication.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An analyzing system including a detector system for measuring electrocardiograms, pulses and voice sounds at the same time, the detector system comprising:
   a flexible framework;
   a electrocardiogram detector comprising at least two electrodes, wherein these two electrodes are integrated by the flexible framework and the flexible framework can pressurize to keep the electrodes in contact with a subject for detecting electrocardiograms from the subject's neck; and
   a pulse detector comprising at least a microphone, wherein the microphone is disposed on the subjects' neck adjacent to the subject's carotid arteries and collects pulse sounds and vibrations from the carotid arteries and voice sounds from the subject's vocal chord, and wherein the microphone is integrated with the electrodes by the flexible framework and the flexible framework can pressurize to keep the microphone in contact with the subject, wherein the electrocardiogram detector and the pulse detector further comprise at least an amplifier, a filter and a analog-to-digital converter, so that the collected pulse sounds, vibrations and voice sounds are transformed into electrical signals and the electrocardiograms and transformed electrical signals are process and outputted as digital signals; and
   the analyzing system further comprising
   a computing system for analyzing the digital signals from the electrocardiograms, pulse sounds, vibrations and voice sounds, wherein the computing system detect and mark heart beats from the digital signals from the electrocardiograms, pulse sounds and vibrations and perform digital signal processing processes to characterize heart rate variability with quantified parameters, thus obtaining an analyzing result.

2. The analyzing system as claimed in claim 1, wherein the computing system can be selected from one of the following group consisting of a personal computer, a personal digital assistant, a microchip included in a mobile phone and a microchip included within a watch.

3. The analyzing system as claimed in claim 1, wherein the analyzing result can be directly shown to a user or be transmitted through a network or a wireless communication technique to another computing system for storage and analysis.

4. The analyzing system as claimed in claim 2, wherein the digital signal processing processes at least include frequency-domain analysis, time-domain analysis and non-liner analysis, and wherein the quantified parameters at least include power spectrum density (PSD), high frequency (HF), low frequency (LF), total power (TP) and HF/LF.

5. The analyzing system as claimed in claim 1, wherein the analyzing system can be applied for evaluating autonomic nervous system functions, levels of anesthesia, brain death, aging and gender variation.

6. A detector system for measuring electrocardiograms, pulses and voice sounds at the same time, comprising:
   a flexible framework;
   a electrocardiogram detector comprising at least two electrodes, wherein these two electrodes are integrated by the flexible framework and the flexible framework can pressurize to keep the electrodes in contact with a subject for detecting electrocardiograms from the subject's neck; and
   a pulse detector comprising at least a microphone, wherein the microphone is disposed on the subjects' neck adjacent to the subject's carotid arteries and collects pulse sounds and vibrations from the carotid arteries and voice sounds from the subject's vocal chord, and wherein the microphone is integrated with the electrodes by the flexible framework and the flexible framework can pressurize to keep the microphone in contact with the subject, wherein the electrocardiogram detector and the pulse detector further comprise at least an amplifier, a filter and a analog-to-digital converter, so that the collected pulse sounds, vibrations and voice sounds are transformed into electrical signals and the electrocardiograms and transformed electrical signals are process and outputted as digital signals.

7. The detector system as claimed in claim 6, wherein the detector system can be further connected to an analyzing system to process and analyze the digital signals, the analyzing system further comprising:
   a computing system for analyzing the digital signals from the electrocardiograms, pulse sounds, vibrations and voice sounds, wherein the computing system detect and mark heart beats from the digital signals from the electrocardiograms, pulse sounds and vibrations and perform digital signal processing processes to characterize heart rate variability with quantified parameters, thus obtaining an analyzing result.

8. The detector system as claimed in claim 7, wherein the computing system can be selected from one of the following group consisting of a personal computer, a personal digital assistant, a microchip included in a mobile phone and a microchip included within a watch.

9. The detector system as claimed in claim 7, wherein the analyzing result can be directly shown to a user or be transmitted through a network or a wireless communication technique to another computing system for storage and analysis.

10. The detector system as claimed in claim 7, wherein the digital signal processing processes at least include frequency-domain analysis, time-domain analysis and non-liner analysis, and wherein the quantified parameters at least include power spectrum density (PSD), high frequency (HF), low frequency (LF), total power (TP) and HF/LF.

11. A method for measuring electrocardiograms, pulses and voice sounds at the same time, comprising:
   collecting electrocardiograms, pulses and voice sounds from a subject's neck at the same time;
   transforming the pulses and voice sounds into electrical signals;
   amplifying and processing the electrocardiograms and electrical signals from the pulses and voice sounds with a plurality of filters;
   converting the electrocardiograms and electrical signals from the pulses and voice sounds into digital signals by a analog-to-digital converter;
   outputting the digital signals to a processor; and
   analyzing the digital signals by the processor to obtain an analyzing result.

12. The method of claim 11, wherein the processor has a digital signal processing unit that performs at least frequency-domain analysis, time-domain analysis and non-liner analysis, to obtain quantified parameters including power spectrum density (PSD), high frequency (HF), low frequency (LF), total power (TP) and HF/LF.

13. The method of claim 12, wherein the processor can be selected from one of the following group consisting of a personal computer, a personal digital assistant, a microchip included in a mobile phone and a microchip included within a watch.

14. The method of claim 11, wherein the method further comprises outputting the analyzing result to a display monitor after analyzing the digital signals.

15. The method of claim 11, wherein the method further comprises outputting the analyzing result through a network or a wireless communication technique to another computing system for storage and analysis.

16. The method of claim 11, wherein a singular detector system is used to collect the electrocardiograms, pulses and voice sounds from the subject's neck at the same time and wherein the detector system comprises at least one microphone for collecting the pulses and voice sounds and two electrodes for collecting electrocardiograms.

17. The method of claim 11, wherein the analyzing result can be applied for evaluating autonomic nervous system functions, levels of anesthesia, brain death, aging and gender variation.

* * * * *